(12) United States Patent
Lilley

(10) Patent No.: US 6,599,958 B2
(45) Date of Patent: *Jul. 29, 2003

(54) RADIATION CURABLE NAIL COATINGS

(75) Inventor: Pamela H. Lilley, Prescott, AZ (US)

(73) Assignee: Gel Products, Inc., Dewey, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/912,816

(22) Filed: Jul. 24, 2001

(65) Prior Publication Data

US 2002/0010226 A1 Jan. 24, 2002

Related U.S. Application Data

(62) Division of application No. 09/466,986, filed on Dec. 17, 1999.

(51) Int. Cl.$^7$ ............................. C08F 2/46; C08F 2/50
(52) U.S. Cl. ....................... 522/182; 522/96; 522/18; 522/64; 522/49; 522/50; 522/38; 522/120; 522/121; 522/151; 522/152; 522/173; 522/174; 424/61; 424/401; 252/182.13; 252/182.18; 252/182.22; 252/182.29
(58) Field of Search ..................... 522/182, 96, 18, 522/64, 49, 50, 38, 120, 121, 173–174, 151, 152; 424/61, 401; 252/182.13, 182.18, 182.22, 182.29

(56) References Cited

U.S. PATENT DOCUMENTS

| | | | |
|---|---|---|---|
| 2,979,061 A | 4/1961 | Greenman | 132/73 |
| 3,629,187 A | 12/1971 | Waller | 260/41 R |
| 3,709,866 A | 1/1973 | Waller | 260/27 R |
| 4,089,763 A | 5/1978 | Dart et al. | 204/159.23 |
| 4,174,307 A | 11/1979 | Rowe | 204/159.19 |
| 4,189,365 A | 2/1980 | Schmitt et al. | 204/159.23 |
| 4,260,701 A | 4/1981 | Lee, Jr. | 525/303 |
| 4,596,260 A | 6/1986 | Giuliano | 132/73 |
| 4,600,030 A | 7/1986 | Newman | 132/88.5 |
| 4,666,952 A * | 5/1987 | Henne et al. | 522/10 |
| 4,682,612 A | 7/1987 | Giuliano | 132/73 |
| 4,690,369 A | 9/1987 | Giuliano | 249/55 |
| 4,704,303 A | 11/1987 | Cornell | 427/53.1 |
| 4,718,957 A | 1/1988 | Sensenbrenner | 156/152 |
| 4,721,735 A * | 1/1988 | Bennett et al. | 522/71 |
| 4,745,003 A | 5/1988 | Sirkoch et al. | 427/54.1 |
| 4,766,005 A | 8/1988 | Montgomery et al. | 427/4 |
| 4,813,875 A | 3/1989 | Hare | 433/214 |
| 4,844,102 A | 7/1989 | Repensek et al. | 132/73 |
| 4,846,165 A | 7/1989 | Hare et al. | 128/156 |
| 4,863,993 A | 9/1989 | Montgomery | 524/854 |
| 4,867,680 A | 9/1989 | Hare et al. | 433/37 |
| 5,071,888 A * | 12/1991 | Kubota | 522/10 |
| 5,118,495 A | 6/1992 | Nafziger et al. | 424/61 |
| 5,177,120 A | 1/1993 | Hare et al. | 523/109 |
| 5,229,431 A | 7/1993 | Pinchuk | 521/159 |
| 5,415,903 A | 5/1995 | Hoffman et al. | 428/15 |
| 5,453,451 A | 9/1995 | Sokol | 522/42 |
| 5,456,905 A | 10/1995 | Valenty | 424/61 |
| 5,516,509 A | 5/1996 | Marr-Leisy et al. | 424/61 |
| 5,637,292 A | 6/1997 | Thomas | 424/61 |
| 5,662,891 A | 9/1997 | Martin | 424/61 |
| 5,708,052 A | 1/1998 | Fischer et al. | 523/116 |
| 5,785,958 A | 7/1998 | Sirdesai et al. | 424/61 |
| 5,792,447 A | 8/1998 | Socci et al. | 424/61 |
| 5,824,373 A | 10/1998 | Biller et al. | 427/474 |
| 5,965,111 A | 10/1999 | Ellingson et al. | 424/61 |
| 5,985,951 A | 11/1999 | Cook | 522/88 |

* cited by examiner

*Primary Examiner*—James J. Seidleck
*Assistant Examiner*—Sanza L McClendon
(74) *Attorney, Agent, or Firm*—Deborah A. Peacock; Peacock, Myers & Adams, PC

(57) ABSTRACT

Light cured nail coatings that are applied to natural nails and/or artificial nail-tips for cosmetic purposes. An optional bond-enhancing compound can be used to strengthen the bond between the light curable coatings and the natural nail. Also, finishing compounds may be used to clean the surface of the uv curable coatings resulting in a high-gloss shine. The methods of applying uv-radiation curable nail coatings, bond-enhancing compounds, and finishing compounds to artificial nail-tips and natural nail are also discussed.

74 Claims, No Drawings

RADIATION CURABLE NAIL COATINGS

CROSS-REFERENCE TO RELATED APPLICATIONS

This application is a divisional application of U.S. patent application Ser. No. 09/466,986, entitled "Radiation Curable Nail Coatings," to Pamela H. Lilley, filed on Dec. 17, 1999, and the specification thereof is incorporated herein by reference.

BACKGROUND OF THE INVENTION

1. Field of the Invention (Technical Field)

The present invention relates to visible and ultraviolet ("uv") radiation curable nail (e.g. fingernail and toe nail) coatings, compounds used to enhance the bonding between the radiation curable coatings and natural nail and finishing compounds used to clean the surface of the radiation curable coatings. The present invention also relates to the methods of applying radiation curable nail coatings, bond-enhancing compounds, and finishing compounds to artificial nail-tips and natural nails.

2. Background Art

Light curable nail coatings are disclosed in Billings, U.S. Pat. No. 5,194,292, entitled "Method of Drying and Bonding Nail Polish;" Cornell, U.S. Pat. No. 4,704,303, entitled "Nail Extension Composition;" and Guiliano, U.S. Pat. No. 4,682,612, entitled "Novel Process and Article for Preparing Artificial Nails." The '292 patent describes a method of protecting common nail polish by applying a light-curable clear coating over the polished nail. The '303 patent describes a coating composition based on an aliphatic or cycloaliphatic hydrocarbon urethane diacrylate or methacrylate having a molecular weight of 250 to 500 and a viscosity of 5,000 to 30,000 cps. Radiation in the visible region is used to cure the '303 patent coatings. The '612 patent describes an organic solvent-free photocurable composition which has at least one liquid monomer in which an acrylated urethane oligomer is dissolved and crosslinked upon cure. Radiation in the uv region is used to cure the '612 patent coatings. None of these patents disclose the use of Bisphenol A Diglycidyl Methacrylate ("BISGMA") based urethane resin.

Problems associated with the prior light curable nail coatings include the tendency of the coatings to run on the nail during application due to low resin viscosities. Consequently, the prior art coatings tend to run onto the cuticle or other unwanted areas and cause lifting of the coating with time. In contrast, the present invention comprises a creamy consistency with a viscosity of between approximately 20,000–80,000 cps. The higher viscosity of the mixtures of the present invention allows the mixtures to be brushed onto the nail or nail tip without significant displacement during the application process, thus reducing the chance of lifting.

Another problem with the prior light curable nail coatings is the use of urethane resins made with high levels of toxic catalysts, which pose a great risk of skin sensitization. In contrast, the urethane resins used in the present invention require relatively low levels of catalyst, and thus do not generally cause skin sensitization in the general population.

Another problem with the prior light curable nail coatings is that over time the coatings tend to lift from the natural nail. The present invention overcomes this problem through the optional application of pre-bond compounds which enhance the bond between the natural nail and the coatings of the present invention as well as the prior light curable nail coatings.

Another problem with the prior light curable nail coatings is that upon curing the surface of the coating becomes sticky and rough due to air inhibition. Generally, ethyl alcohol is then applied to the coating surface to remove the undesirable air inhibited layer. The present invention includes various compounds that improve the final appearance and characteristics of the coated nail.

SUMMARY OF THE INVENTION
(DISCLOSURE OF THE INVENTION)

The present invention is of a composition that is applied to natural nails and artificial nail tips. The composition comprises a polymeric compound, a photoinitiator, and a photoaccelerator. In one embodiment the composition comprises: between approximately 30 and 98 percent by weight, preferably between approximately 60 to 95 percent by weight, of polymeric compound; between approximately 0.05 and 10 percent by weight, preferably between approximately 0.1 and 5 percent by weight, of photoinitiator; and between approximately 0.1 and 5 percent by weight, preferably between approximately 0.25 and 1 percent by weight, of photoaccelerator. In the preferred embodiment, the polymeric compound or compounds comprise acrylates and/or methacrylates, the photoinitiator comprises phosphinates and phosphine oxides, and the photoaccelerator comprises aliphatic amines and aromatic amines, preferably ethyl 4-dimethylaminobenzoate, butoxyethyl dimethylaminobenzoate, octyl-para-dimethylaminobenzoate, and/or ethyl dimethylaminoethyl methacrylate.

In another embodiment the composition may optionally comprise a coupling agent. The composition comprising between approximately 0.01 and 0.5 percent by weight, preferably between approximately 0.05 and 0.15 percent by weight, of coupling agent. In the preferred embodiment, the coupling agent utilized comprises an organo-metallic, preferably an organo-titanate coupling agent such as isopropyldimethylacrylisiostearoyl titanate, tetraisopropyldi(dioctyl) phosphito titanate, neopentyl(diallyl)oxy,tri(dodecyl) benzene-sulfonyl titanate, and neopentyl(diallyl)oxy, trineodecanonyl titanate.

In another embodiment the composition may optionally comprise at least one additive such as a plasticizers, secondary photoinitiators, colorants, dyes, inhibitors, fillers, fibers, and/or adhesion promoting polymers. The composition comprising between approximately 0 and 50 percent by weight, preferably between approximately 1 and 20 percent by weight, of additive. The composition may optionally comprise: a plasticizer such as phthalates, adipates, and/or sulfonamides; a secondary photoinitiator such as camphorquinone, benzil dimethylketal, and/or benzophenone; a colorant such as barium, calcium, aluminum lakes, iron oxides, talcs, carmine, titanium dioxide, chromium hydroxides, ferric ferrocyanide, ultramarines, titanium dioxide coated mica platelets, and/or bismuth oxychlorides; an inhibitor such as hydroquinone, methyl ether hydroquinone, and/or butylated hydroxy toluene; a filler such as mineral fillers and/or polymeric fillers; and an adhesion promoting polymer such as methacryoyloxy ethyl phthalate.

In another embodiment the composition comprises a BISGMA urethane, a polyether, methacrylated urethane, a photoinitiator, and a photoaccelerator. In one embodiment, the composition comprises: between approximately 30 and 90 percent by weight, preferably between approximately 50 to 70 percent by weight, of BISGMA urethane; between approximately 0.5 to 50 percent by weight, preferably between approximately 10 to 40 percent by weight, of methacrylated urethane; between approximately 0.05 to 10 percent by weight, between approximately 0.5 to 5 percent by weight, of photoinitiator; and between approximately 0.1 and 5 percent by weight, preferably between approximately 0.25 and 1 percent by weight, of photoaccelerator. In the preferred embodiment, the composition comprises: a mathacrylated urethane having a viscosity greater than 100,000 cps; a photoinitiator such as camphorquinone, ethyl 2,4,6-trimethylbenzoyldiphenylphosphine oxide, benzildimethyl ketal, and/or benzophenone; and a photoaccelerator such as aliphatic amines and aromatic amines, preferably ethyl 4-dimethylaminobenzoate, butoxyethyl dimethylaminobenzoate, octyl-para-dimethylaminobenzoate, and ethyl dimethylaminoethyl methacrylate.

In another embodiment the composition may optionally comprise a coupling agent. The composition comprising between approximately 0.01 and 0.5 percent by weight, preferably between approximately 0.05 and 0.15 percent by weight, of coupling agent. In the preferred embodiment, the coupling agent utilized comprises an organo-metallic, preferably an organo-titanate coupling agent such as isopropyldimethylacrylisiostearoyl titanate, tetraisopropyldi(dioctyl) phosphito titanate, neopentyl(diallyl)oxy,tri(dodecyl) benzene-sulfonyl titanate, and neopentyl(diallyl)oxy, trineodecanonyl titanate.

In another embodiment the composition may optionally comprise at least one additive such as a plasticizers, secondary photoinitiators, colorants, dyes, inhibitors, fillers, fibers, and/or adhesion promoting polymers. The composition comprising between approximately 0 and 50 percent by weight, preferably between approximately 1 and 20 percent by weight, of additive. The composition may optionally comprise: a plasticizer such as phthalates, adipates, and/or sulfonamides; a secondary photoinitiator such as camphorquinone, benzil dimethylketal, and/or benzophenone; a colorant such as barium, calcium, aluminum lakes, iron oxides, talcs, carmine, titanium dioxide, chromium hydroxides, ferric ferrocyanide, ultramarines, titanium dioxide coated mica platelets, and/or bismuth oxychlorides; an inhibitor such as hydroquinone, methyl ether hydroquinone, and/or butylated hydroxy toluene; a filler such as mineral fillers and/or polymeric fillers; and an adhesion promoting polymer such as methacryoyloxy ethyl phthalate.

A primary object of the present invention is to provide hard and durable coatings for the cosmetic industry, particularly for the cosmetic nail industry.

A further object of the invention is to provide high gloss and smooth finishing compounds that are applied to the coated fingernails after curing.

A further object of the invention is to provide pre-bonding compounds that are applied to the natural nail to enhance bonding between the nail coatings and the natural nail.

A primary advantage of the present invention is that the coating compounds are of sufficient viscosity such that the compounds do not tend to run off the nail and onto the finger or toe.

Another advantage of the present invention is that the coating compounds result in a strong and durable bond to both artificial nail tips and natural nails.

Another advantage of the present invention is that the coating compounds comprise chemical compounds that exhibit a low degree of skin sensitivity.

Another advantage of the present invention is that a pre-bonding compound may be used in conjunction with the coating compounds.

Another advantage of the present invention is that a finishing compound may be used in conjunction with the coating compounds to clean the surface of the coating and apply a polished, high gloss surface.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (BEST MODES FOR CARRYING OUT THE INVENTION)

The present invention relates to actinic (visible and uv) radiation curable coating compositions used to coat artificial nail tips and strengthen and coat natural nails. The compositions are applied to the natural nail or to the natural nail and a pre-formed nail tip that is attached to the natural nail. The coatings react with actinic radiation, even in highly colored compositions. The coating compositions can be formulated in clear, opaque white, translucent colors and opaque colors, and cure, in some cases, in less than two minutes with uv radiation. The coating compounds are either polymeric or urethane based. In the case of the polymeric compounds the term "polymeric" or "polymer" as used throughout the specification and claims, is intended to include monomers, oligomers, and polymers.

In one embodiment of the invention, a biocompatible solvent-based adhesive resin (pre-bond compound) is used to enhance the bond between the radiation curable nail coatings and the natural nail. The natural nails are preferably prepared by filing, and a thin coat of the solvent-based adhesive resin is applied to the surface of the natural nail beginning at the cuticle area. The solvent evaporates leaving a sticky layer of the adhesive. The radiation curable nail coating is then applied to the adhesive. In another embodiment incorporating artificial nail tips, the artificial nail tip is attached to the natural nail as is known in the art. A thin coat of the solvent-based adhesive resin is applied to the surface of the natural nail beginning at the cuticle area and ending at the front edge of the nail tip. There is no need to apply the adhesive resin to the surface of the nail tip. The solvent evaporates leaving a sticky layer of the adhesive. The radiation curable nail coating is then applied to the adhesive on the surface of the natural nail as well as the nail tip. The use of the adhesive resin enhancer prevents lifting of the cured coating from the natural nail, adding longevity and beauty.

The pre-bond compounds can also be used to enhance the adhesive properties of polymeric filler compounds used to treat animal hoofs and claws. In one application, the pre-bond compound is initially added to a crack or hole in the hoof, e.g., a horse hoof, and the solvent is allowed to partially evaporate resulting in a tacky surface. The polymeric filler compounds are then added to fill the voids in the hoof or claw. The hoof or claw can then be filed to the desired shape and appearance.

Pre-bond Compounds

The present invention comprises pre-bond compounds that are applied to the natural nail to enhance the adhesive properties of the coating compounds of the invention. The pre-bond compounds comprise an acrylate based polymer, preferably an aromatic acid methacrylate, in a biocompatible solvent. The preferred aromatic acid methacrylate is commercially available as Sarbox SB 500E50 from Sartomer Company located in Exton, Pa. Sarbox SB 500E50 is a proprietary aromatic acid methacrylate half ester in ethoxylated trimethylolpropane triacrylate monomer. The acid methacrylate-triacrylate monomer mixture is present in the composition between approximately 2–30% by weight and preferably between approximately 5–20% by weight. In another embodiment hydrogenated rosin is added to the solvent and acrylate polymer mixture. The preferred hydrogenated rosin is commercially available in the form of a glycerol ester from Hercules, formulated as SORAL 85 synthetic resin, and is ground to a powder prior to the addition. The hydrogenated rosin, if added, is present in the composition between approximately 2–30% by weight and preferably 5–20% by weight. The solvent in the composition is biocompatible and evaporates rapidly after being applied to the natural nail. It may be a single organic solvent or blend of organic solvents. The solvent is preferably selected from the group consisting of alcohols, ketones and esters. In the preferred embodiment, the biocompatible solvent is acetone and comprises between approximately 50–95% by weight and preferably between approximately 60–80% by weight, of the composition.

The pre-bond compounds are used in conjunction with the coatings of the present invention to greatly enhance the bonding of the coatings to the natural nail. As a result, lifting of the coating at the cuticle area is significantly reduced. The following pre-bond compositions, useful in accordance with the present invention, are shown in Table 1 in varying percentages. Composition 1 describes a pre-bond composition which gives improved adhesion of the radiation cured coating to natural nails. Composition 2 has more surface tackiness after application and evaporation. Composition 2 gives greatly improved adhesion of the radiation cured coating to the natural nail with little or no lifting during normal wear.

TABLE 1

Pre-Bonding Compositions (grams)

| Composition | 1 | 2 |
|---|---|---|
| Acetone | 8.52 | 52.43 |
| Sarbox 500E50 | 1.52 | 11.18 |
| Hydrogenated Rosin | — | 11.33 |

Coating Compounds

The present invention relates to actinic radiation, preferably uv radiation, curable compounds used to coat natural nails and pre-formed artificial nail tips. The nail tips are attached to the natural nail with a known cyanoacrylate gel compound (e.g. see Cornell U.S. Pat. No. 4,704,303). The coatings of the present invention are durable and do not result in skin sensitivity in the majority of the population. In the preferred embodiment, the coating compounds comprise: (a) acrylate or methacrylate polymers; (b) a photoinitiator, preferably a phosphinate or phosphine oxide photoinitiator; and (c) a photoaccelerator, preferably an aliphatic or aromatic amine photoaccelerator such as ethyl 4-dimethylaminobenzoate, butoxyethyl dimethylaminobenzoate, octyl-para-dimethylaminobenzoate, and ethyl dimethylaminoethyl methacrylate. The coating compounds may further comprise a coupling agent, preferably, a titanate coupling agent, and various other additives such as plasticizers, other photoinitiators, colorants, dyes, inhibitors, fillers, fibers, and adhesion promoting monomers.

In one embodiment, the composition preferably comprises: 1) between approximately 30–99% by weight and preferably between approximately 60–95% by weight of component (A); 2) between approximately 0.05–10% by weight and preferably between approximately 0.1–5% by weight of component (B); and 3) between approximately 0.1–5% by weight and preferably between approximately 0.25–1% by weight of component (C). The one embodiment may further comprise between approximately 0.01–0.5% by weight and preferably between approximately 0.05–0.15% by weight of a coupling agent (component (D)); and between approximately 0–50% by weight and preferably between approximately 1–20% by weight of other additives (component (E)).

Component (A) is preferably acrylate or methacrylate polymers. Component (B) is preferably an acyl phosphine oxide such as 2,4,6-trimethyl benzoyldiphenylphosphine oxide or an alkyl phosphinate such as ethyl 2,4,6-trimethyl benzoylphenylphosphinate, commonly available from BASF. Component (C) is preferably an aliphatic or aromatic amine photoaccelerator such as ethyl 4-dimethylamino benzoate, butoxyethyl dimethylaminobenzoate, octyl-para-dimethylaminobenzoate or ethyl dimethyl aminoethyl methacrylate. The preferred coupling agent, component (D), is an organic titanate coupling agent such as a class of neoalkoxy titanates available from Kenrich Petrochemicals. Additional and optional additives, component (E), may include: plasticizers such as the phthalates, adipates and sulfonamides; other photoinitiators such as camphorquinone and benzil dimethylketal, benzophenone; inhibitors such as hydroquinone, methyl ether hydroquinone and butylated hydroxy toluene; mineral and polymeric fillers; fibers; adhesion promoting monomers such as methacryoyloxy ethyl phthalate; and colorants such as barium, calcium and aluminum lakes, iron oxides, talcs, carmine, titanium dioxide, chromium hydroxides, ferric ferrocyanide, ultramarines, titanium dioxide coated mica platelets and bismuth oxychlorides.

In a second embodiment, the coating composition is based on the combination of a BISGMA urethane and an aliphatic methacrylated urethane with a preferred viscosity greater than 100,000 cps. The BISGMA based nail coating, even a coating that is heavily pigmented, reacts with uv radiation. A coat of the material cures with a standard ultraviolet nail light in less than two minutes. Moreover, it cures with visible light, such as from a dental curing unit, in less than 20 seconds.

Another embodiment of the present invention preferably comprises: 1) a resin, preferably a BISGMA urethane resin, prepared from an adduct of BISGMA and an aliphatic or cycloaliphatic hydrocarbon diisocyanate (component (A)); 2) a polyether based, methacrylated aliphatic urethane oligomer with a viscosity greater than 80,000 cps (component (B)); 3) a photoinitiator (component (C)); and 4) a photoaccelerator (component (D)). This second embodiment may further comprise a coupling agent (component (E)) and various other additives such as plasticizers, colorants, dyes, inhibitors, fillers, fibers, adhesion promoting monomers and crosslinking monomers (components (F)). The coating preferably comprises between approximately 30–90% by weight of and preferably between approximately 50–70% by weight of component (A); between approximately 0.5–50% by weight and preferably between approximately 10–40% by weight of component (B); between approximately 0.05–10% by weight and preferably between approximately 0.5–5% by weight of component (C); and between approximately 0.1–5% by weight and preferably between approximately 0.25–1% by weight of component (D). The coating may further comprise a coupling agent (component (E)) in an amount of between approximately 0.01–0.5% by weight and preferably between approximately 0.05–0.15% by weight. Further, the composition may optionally comprise between approximately 1–50% and preferably between approximately 5–20% by weight of any one or combination of components (F).

The BISGMA based urethane resin is preferably prepared by reacting the hydroxyl functions of BISGMA with a hydrocarbon diisocyanate. In the preferred embodiment, the BISGMA is diluted with dimethacrylate monomers, a catalyst is added and then the diisocyanate compound is slowly added. The reaction mixture is heated (approximately 55° C.) until all the diisocyanate has reacted to the BISGMA urethane. BISGMA can be purchased from Esstech, and is also sold as Nupol 46-4005 from Cook Composites and Polymers. BISGMA is a very thick, sticky, liquid which must be diluted with dimethacrylate monomers prior to the addition of the diisocynate. The dimethacrylate monomers are well suited for the dilution step because they exhibit relatively low volatility and low odor. The dimethacrylate monomers also serve as crosslinking agents in the urethane resin. Suitable dimethacrylate monomers are diethylene glycol dimethacrylate, 1,6-hexane diol dimethacrylate, triethylene glycol dimethacrylate, ethoxylated bisphenol A dimethacrylate, polyethylene glycol dimethacrylate, and 1,4-butanediol dimethacrylate. The final urethane resin comprises between approximately 30–70% dimethacrylate monomers based on the weight of the BISGMA adduct in the urethane resin.

Urethane catalysts useful in the invention are tin compounds such as dibutyl tin dilaureate and stannous octoate. They are used at levels between approximately 0.005–0.10% by weight in the urethane resin. The tin compound is added to the mixture of BISGMA and dimethacrylate monomers and mixed. The diisocyanate is an aliphatic or cycloaliphatic hydrocarbon such as heptyl diisocyanate, trimethylhexamethylene diisocyanate, or isophorone diisocyanate. The diisocyanate is slowly added to the BISGMA, dimethacrylate monomer and catalyst mixture to form the urethane. The diisocyanate is used at levels of between approximately 5–12% by weight of the urethane resin. Alternatively, the diisocynate may be diluted with dimethacrylate monomer to control the exothermic urethane reaction. Once the urethane reaction is completed, a small amount of inhibitor, preferably butylated hydroxy toluene, in an amount of between approximately 0.01–0.10% by weight, is added.

The polyether based methacrylated aliphatic urethane oligomer with a viscosity greater than 80,000 cps is then mixed with the BISGMA based urethane. The photoinitiator is then added, preferably camphorquinone, ethyl 2,4,6-trimethylbenzoylphenylphosphinate, 2,4,6-trimethylbenzoyl diphenylphosphine oxide, benzil dimethyl ketal and/or benzophenone. The remaining ingredients are also added: plasticizers such as phthalates, adipates, and sulfonamides; aliphatic or aromatic amine photoaccelerators such as ethyl 4-dimethylaminobenzoate, butoxyethyl dimethylaminobenzoate, octyl-para-dimethylaminobenzoate, and ethyl dimethylaminoethyl methacrylate; titanate coupling agents such as isopropyl dimethacryl isostearoyl titanate, tetraisopropyl di(dioctyl) phosphito titanate, neopentyl(diallyl)oxy-tri(dodecyl) benzene-sulfonyl titanate, and neopentyl(diallyl)oxy-trineodecanonyl titanate; inhibitors such as hydroquinone, methyl ether hydroquinone and butylated hydroxy toluene; mineral and polymeric fillers; fibers; adhesion promoting monomers such as methacryoyloxy ethyl phthalate; colorants such as barium, calcium, aluminum lakes, iron oxides, talcs, carmine, titanium dioxide, chromium hydroxides, ferric ferrocyanide, ultramarines, titanium dioxide coated mica platelets, and bismuth oxychlorides.

Finishing Compounds

The present invention comprises nail finishing compounds that complement the actinic radiation curable coatings. After the coating has been applied and cured with actinic radiation, oxygen inhibition causes the surface of the coating to become tacky. Typically, isopropyl alcohol is used to remove the sticky layer. As an alternative, the compositions of the finishing compounds may be applied with a cotton swab or pad, or sprayed directly onto the nail to remove the sticky surface. The nail is then rubbed, for example, with a clean cloth, resulting in a clean smooth surface. A high gloss surface results using the finishing compounds of the present invention as compared to using 100% isopropyl alcohol. The nail treatment may be considered complete at this point. If higher gloss is desired, a topcoat of a solvent-based cellulose material may be applied to complete the procedure.

The finishing compounds are applied to the cured coating to provide a sleek, high gloss surface, Table 2. The finishing compounds preferably comprise: 1) between approximately 30–90% by weight and preferably between approximately 50–80% by weight, of a biocompatible solvent such as acetone, ethyl alcohol, ethyl acetate, isopropyl alcohol, and methyl ethyl ketone; 2) between approximately 5–40% by weight and preferably between approximately 10–30% by weight, of a plasticizer such as phthalates, adipates and sulfonamides, or an oil, such as castor oil; and 3) between approximately 5–30% by weight and preferably between approximately 10–20% by weight, of a lanolin based compound such as PEG-75 lanolin, hydroxylated lanolin, hydrogenated lanolin, and other lanolin derivatives. A fragrance, such as lavender oil, may also be added to make this composition more appealing to the consumer. Some representative compositional mixtures for the finishing compounds are shown in Table 2.

Finishing compound 3 comprises approximate equal proportions by weight of isopropyl alcohol and the plasticizer, dioctyl adipate. Finishing compound 4 comprises approximate equal proportions by weight of ethyl alcohol and the plasticizer, dioctyl adipate with smaller amounts of a lanolin based compound. Finishing compound 5 is similar to finishing compound 4 with the exception that isopropyl alcohol is substituted for the ethyl alcohol. Finishing compound 6 substitutes castor oil for the plasticizer in the prior compositions and also includes a fragrant compound.

TABLE 2

| Finishing Compounds (grams) | | | | |
|---|---|---|---|---|
| Composition | 3 | 4 | 5 | 6 |
| Ethyl Alcohol | — | 8.56 | — | — |
| Isopropyl alcohol | 3.82 | — | 3.73 | 49.83 |
| Lanolin PEG-75 | — | 1.25 | 0.55 | 8.97 |
| Dioctyl Adipate | 3.92 | 11.50 | 4.97 | — |
| Castor Oil | — | — | — | 8.66 |
| Lavender Oil | — | — | — | 0.62 |

Method of Applying Compounds to Natural Nails and Nail-tips

To apply the compounds of the present invention to a natural nail, the nail is preferably filed on the top surface to remove oils and create a surface for bonding. A bond-enhancing compound of the present invention is applied to the entire surface of the nail, preferably beginning at the cuticle. The solvent in the pre-bond finishing compound is allowed to evaporate over a given period, leaving a tacky surface. An optional actinic radiation curable white tipping coating is then applied to the ends of the nail and cured if the French manicure look is desired. A clear or light pink coating compound is applied to the nail, preferably starting at the cuticle and moving toward the white tipping, and cured. The coated nail is then filed to a smooth surface. A clear coating compound is applied over the entire nail surface and cured. Application of a second clear coat is optional. The finishing compound is applied to remove the top sticky layer and the coated nail is buffed to a high gloss shine.

The method of applying the colored coating compounds is similar to the methods described above for the clear-white tipped nails except the second final clear coat is replaced with a colored coating. Application of an optional second colored coat is applied for best results.

INDUSTRIAL APPLICABILITY

The invention is further illustrated by the following non-limiting examples with their respective chemical components listed in grams (see Table 3).

TABLE 3

| Composition | 7 Prior Art | 8 Prior Art | 9 | 10 | 11 | 12 | 13 | 14 | 15 |
|---|---|---|---|---|---|---|---|---|---|
| UDMA resin | 3.01 | 3.79 | 12.56 | — | — | — | — | — | — |
| Ethoxylated BPADMA | 4.04 | 4.61 | 6.00 | — | — | — | — | — | — |
| Benzildimethyl ketal | .0316 | — | .04 | .0771 | .0211 | .1920 | .0470 | .0392 | .0283 |
| Butoxyethyldimethyl amino-benzoate | .09 | — | — | — | — | — | — | — | — |
| Dimethylaminoethyl methacrylate | — | .13 | — | — | — | .51 | .13 | .1074 | .0776 |
| Octyl-para-dimethyl aminobenzoate | — | — | .14 | .2264 | .0649 | — | — | — | — |
| Ethyldimethylamino benzoate | — | — | — | — | — | — | — | .0311 | — |
| Ethyl 2,4,6-trimethyl benzoylphenylphosphinate | — | .09 | .17 | .2459 | .0674 | .52 | .13 | .11 | .08 |
| Neoalkoxy titanate | — | — | .02 | .0300 | .0084 | .11 | .0300 | .0248 | .0179 |
| D & C Red #33 | — | — | — | — | .0136 | — | — | — | — |
| D & C Red #6 Barium Lake | — | — | — | — | — | — | — | .0495 | — |
| D & C Red #7 Calcium Lake | — | — | — | — | — | — | — | .1127 | — |
| Ext. D & C Violet #2 | — | — | — | — | — | — | — | .0015 | — |
| Titanium dioxide coated mica platelets | — | — | — | — | — | — | — | — | .0750 |
| Titanium dioxide | — | — | .07 | — | — | — | .0374 | .0300 | .0075 |
| N-ethyl-o & p toluenesulfonamide | — | — | 1.00 | 2.10 | 0.59 | 7.09 | 1.75 | 1.46 | 1.05 |
| Mono(Methacryloyloxyethyl) Phthalate | — | — | — | — | — | 2.67 | .66 | .55 | .40 |
| Methacrylated-aliphatic Urethane Resin | — | — | — | 4.50 | 2.52 | 30.43 | 7.46 | 6.22 | 4.50 |
| BISGMA Urethane Resin of the Invention | — | — | — | 22.83 | 5.15 | 59.8 | 14.54 | 12.13 | 8.77 | optional. The finishing compound is applied to remove the top sticky layer and the coated nail is buffed to a high gloss shine.

To apply the compounds of the present invention to a nail-tip that is attached to natural nail, the nail is filed on the top surface to remove oils and create a surface for bonding. The nail-tip is applied to the natural nail with a glue (e.g. cyanoacrylate glue) known in the art. After the glue has set, the nail-tip is filed. The bond-enhancing compound of the present invention is applied to the natural nail, preferably beginning at the cuticle to the front edge of the nail-tip. It is not necessary to apply the bond-enhancing compound to the surface of the nail tip. An optional actinic radiation curable white tipping coating is applied to the ends of the nail-tip and cured. A clear or light pink coating compound is applied to the entire nail, preferably starting at the cuticle and moving toward the white tipping, and cured. The coated nail is then filed to a smooth surface. A clear coating compound is applied over the entire nail surface and cured. Application of a second clear coat is optional. The finishing compound Compositional mixtures 7 and 8 illustrate typical uv radiation curable resin systems in the art. Compositions 7 and 8 cure under uv light in about two to three minutes. Compositions 9 to 15 illustrate the coating compounds of the present invention. Compositional mixture 9 is a composition which is highly reactive to uv radiation and will cure in less than two minutes, even with a high level of titanium dioxide white pigment. Compositional mixtures 10–12 are coating compositions with the BISGMA urethane resin and the polyether based methacrylated aliphatic urethane resin. The latter resin having a viscosity greater than 80,000 cps. These compositions are easily applied and exhibit a creamy consistency, which do not run on the nail during application, unlike the prior art compositional mixtures 7 and 8. Compositional mixtures 10–12 exhibit clear and translucent pink shades that are easily cured with uv radiation in less than two minutes to a durable nail coating. Compositional mixture 13 is a uv radiation cured opaque white material useful for covering the very end of the natural nail or nail tip to give the French manicure look. Compositional mixture 14 is a very highly colored formulation and compositional mixture 15 is a shimmery or opalescent formula, both of which cure to durable coatings when exposed to uv radiation for approximately two minutes.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A radiation curable natural nail and/or artificial nail tip coating composition comprising:
    a polymer;
    a photoinitiator; and
    a photoaccelerator wherein said photoaccelerator comprises butoxyethyl dimethylaminobenzoate;
    said composition of a sufficient viscosity to be applied to natural nails and artificial nail tips and so as to not run on the nail or nail tip during application.

2. The composition of claim 1 wherein said polymer comprises at least one member selected from the group of acrylates and methacrylates.

3. A radiation curable natural nail and/or artificial nail tip coating composition comprising:
    a polymer;
    a photoinitiator; and
    a photoaccelerator wherein said photoaccelerator comprises octyl-para-dimethylaminobenzoate;
    said composition of a sufficient viscosity to be applied to natural nails and artificial nail tips and so as to not run on the nail or nail tip during application.

4. The composition of claim 3 wherein said polymer comprises at least one member selected from the group of acrylates and methacrylates.

5. A radiation curable natural nail and/or artificial nail tip coating composition comprising:
    a polymer;
    a photoinitiator; and
    a photoaccelerator wherein said photoaccelerator comprises ethyl dimethylamino methacrylate;
    said composition of a sufficient viscosity to be applied to natural nails and artificial nail tips and so as to not run on the nail or nail tip during application.

6. The composition of claim 5 wherein said polymer comprises at least one member selected from the group of acrylates and methacrylates.

7. A radiation curable natural nail and/or artificial nail tip coating composition comprising:
    a polymer;
    a photoinitiator;
    a photoaccelerator; and
    an organometallic coupling agent;
    said composition of a sufficient viscosity to be applied to natural nails and artificial nail tips and so as to not run on the nail or nail tip during application.

8. The composition of claim 7 wherein said polymer comprises at least one member selected from the group of acrylates and methacrylates.

9. The composition of claim 7 wherein said coupling agent comprises an organo-titanate coupling agent.

10. The composition of claim 7 wherein said organo-titanate coupling agent comprises isopropyldimethylacrylisiostearoyl titanate.

11. The composition of claim 7 wherein said organo-titanate coupling agent comprises tetraisopropyldi(dioctyl) phosphito titanate.

12. The composition of claim 7 wherein said organo-titanate coupling agent comprises neopentyl(diallyl)oxy,tri (dodecyl)benzenesulfonyl titanate.

13. The composition of claim 7 wherein said organo-titanate coupling agent comprises neopentyl(diallyl)oxy, tri-neodecanonyl titanate.

14. A radiation curable natural nail and/or artificial nail tip coating composition comprising:
    a polymer;
    a photoinitiator;
    a photoaccelerator; and
    a plasticizer wherein said plasticizer comprises at least one member slected from the group consisting of adipate and sulfonamide;
    said composition of a sufficient viscosity to be applied to natural nails and artificial nail tips and so as to not run on the nail or nail tip during application.

15. The composition of claim 14 wherein said polymer comprises at least one member selected from the group of acrylates and methacrylates.

16. The composition of claim 14 further comprising an organometallic coupling agent.

17. The composition of claim 14 wherein said organometallic coupling agent comprises an organo-titanate coupling agent.

18. A radiation curable natural nail and/or artificial nail tip coating composition comprising:
    a BISGMA urethane;
    a polymer;
    a photoinitiator; and
    a secondary photoinitiator comprising camphorquinone;
    said composition of a sufficient viscosity to be applied to natural nails or artificial nail tips and so as to not run on the nail or nail tip during application.

19. A radiation curable natural nail and/or artificial nail tip coating composition comprising:
    a BISGMA urethane;
    a polymer;
    a photoinitiator; and
    an adhesion promotion polymer comprising methacryoyloxy ethyl phthalate;
    said composition of a sufficient viscosity to be applied to natural nails or artificial nail tips and so as to not run on the nail or nail tip during application.

20. A radiation curable natural nail and/or artificial nail tip coating composition comprising:
    a BISGMA urethane;
    a polymer; and
    a photoinitiator wherein said photoinitiator comprises at least one member selected from the group consisting of phosphinate and phosphine oxide;
    said composition of a sufficient viscosity to be applied to natural nails or artificial nail tips and so as to not run on the nail or nail tip during application.

21. The composition of claim 20 wherein said polymer comprises a urethane.

22. The composition of claim 21 wherein said urethane comprises a polyether, methacrylated urethane.

23. The composition of claim 22 wherein said polyether, methacrylated urethane has a viscosity of at least 80,000 cps.

24. The composition of claim 20 further comprising a coupling agent.

25. The composition of claim 24 further comprising an organometallic coupling agent.

26. The composition of claim 25 wherein said organometallic coupling agent comprises an organo-titanate coupling agent.

27. A radiation curable natural nail and/or artificial nail tip coating composition comprising:
   a BISGMA urethane;
   a polymer;
   a photoinitiator; and
   a photoaccelerator comprising at least one member selected from the group consisting of butoxyethyl dimethylaminobenzoate, octyl-paradimethylaminobenzoate, and ethyl dimethylaminoethyl methacrylate;
   said composition of a sufficient viscosity to be applied to natural nails and artificial nail tips and so as to not run on the nail or nail tip during application.

28. A radiation curable natural nail and/or artificial nail tip coating composition comprising:
   a BISGMA urethane;
   a polymer;
   a photoinitiator; and
   an organometallic coupling agent.

29. The composition of claim 28 wherein said organometallic coupling agent comprises an organo-titanate coupling agent.

30. The composition of claim 29 wherein said organo-titanate coupling agent comprises isopropyldimethylacrylisiostearoyl titanate.

31. The composition of claim 29 wherein said organo-titanate coupling agent comprises tetraisopropyldi(dioctyl)phosphito titanate.

32. The composition of claim 29 wherein said organo-titanate coupling agent comprises neopentyl(dially)oxy,tri(dodecyl)benzene-sulfonyl titanate.

33. The composition of claim 29 wherein said organo-titanate coupling agent comprises neopenty(dially)oxy, trineodecanonyl titanate.

34. A radiation curable natural nail and/or artificial nail tip coating composition comprising:
   A BISGMA urethane;
   a polymer;
   a photoinitiator;
   a plasticizer; and
   said composition of a sufficient viscosity to be applied to natural nails and artificial nail tips and so as to not run on the nail or nail tip during application.

35. The composition of claim 34 wherein said polymer comprises a urethane.

36. The composition of claim 35 wherein said urethane comprises a polyether, methacrylated urethane.

37. The composition of claim 34 wherein said photoinitiator comprises a phosphinate or phosphine oxide.

38. The composition of claim 34 further comprising an organometallic coupling agent.

39. The composition of claim 34 wherein said plasticizer comprises a phthalate.

40. The composition of claim 34 wherein said plasticizer comprises a adipate.

41. The composition of claim 34 wherein said plasticizer comprises a sulfonamide.

42. A radiation curable natural nail and/or artificial nail tip coating composition comprising:
   a BISGMA urethane;
   a polymer;
   a photoinitiator; and
   a fiber;
   said composition of a sufficient viscosity to be applied to natural nails and artificial nail tips and so as to not run on the nail or nail tip during application.

43. The composition of claim 42 wherein said polymer comprises a urethane.

44. The composition of claim 43 wherein said urethane comprises a polyether, metacrylated urethane.

45. The composition of claim 42 further comprising a coupling agent.

46. The composition of claim 45 wherein said coupling agent comprises an organometallic agent.

47. The composition of claim 42 further comprising a plasticizer.

48. The composition of claim 47 wherein said plasticizer comprises at least one member selected from the group consisting of a phthalate, adipate and sulfonamide.

49. A radiation curable natural nail and/or artificial nail tip coating composition comprising:
   a BISGMA urethane;
   a polymer;
   a photoinitiator; and
   an adhesion promoting polymer comprising methacryloyloxyethyl phthalate;
   said composition of a sufficient viscosity to be applied to natural nails and artificial nail tips and so as to not run on the nail or nail tip during application.

50. The composition of claim 49 wherein said polymer comprises a urethane.

51. The composition of claim 50 wherein said urethane comprises a polyether, methacrylated urethane.

52. The composition of claim 49 further comprising a plasticizer.

53. A radiation curable natural nail and/or artificial nail tip coating composition comprising:
   a BISGMA urethane;
   a polymer;
   a photoinitiator; and
   a crosslinking polymer;
   said composition of a sufficient viscosity to be applied to natural nails and artificial nail tips and so as to not run on the nail or nail tip during application.

54. The composition of claim 53 wherein said polymer comprises a urethane.

55. The composition of claim 54 wherein said urethane comprises a polyether, methacrylated urethane.

56. The composition of claim 53 wherein said photoinitiator comprises at least one member selected from the group consisting of phosphinate and phosphine oxide.

57. The composition of claim 53 further comprising a plasticizer.

58. The composition of claim 53 further comprising coupling agent.

59. The composition of claim 58 wherein said coupling agent comprises an organometallic coupling agent.

60. The composition of claim 53 further comprising a photoaccelerator.

61. The composition of claim 60 wherein said photoaccelerator comprises at least one member selected from the group consisting of an aromatic amine and an aliphatic amine.

62. A radiation curable natural nail and/or artificial nail tip coating composition comprising:

a BISGMA urethane;

a polymer;

a photoinitiator; and a secondary photoiniator;

said composition of a sufficient viscosity to be applied to natural nails and artificial nail tips and so as to not run on the nail or nail tip during application.

63. The composition of claim 62 wherein said photoinitiator comprises at least one member selected from the group consisting of a phosphinate and phosphine oxide.

64. The composition of claim 62 wherein said secondary photoinitiator comprises camphorquinone.

65. The composition of claim 62 wherein said secondary photoinitiator comprises benzyl dimethylketal.

66. The composition of claim 62 wherein said secondary photoiniator comprises benzophenone.

67. The composition of claim 62 further comprising a photoaccelerator.

68. The composition of claim 67 wherein said photoaccelerator comprises at least one member selected from the group consisting of an aromatic and an aliphatic amine.

69. The composition of claim 62 wherein said polymer comprises a urethane.

70. The composition of claim 69 wherein said urethane comprises a polyether, methacrylated urethane.

71. The composition of claim 70 wherein said polyether, methacrylated urethane has a viscosity of at least 80,000 cps.

72. The composition of claim 62 further comprising a plasticizer.

73. The composition of claim 62 further comprising a coupling agent.

74. The composition of claim 73 wherein said coupling agent comprises an organometallic coupling agent.

* * * * *

UNITED STATES PATENT AND TRADEMARK OFFICE
CERTIFICATE OF CORRECTION

PATENT NO. : 6,599,958 B2
DATED : July 29, 2003
INVENTOR(S) : Pamela H. Lilley

It is certified that error appears in the above-identified patent and that said Letters Patent is hereby corrected as shown below:

<u>Column 14,</u>
Line 16, the word "metacrylated" should read -- methacrylated --.

Signed and Sealed this

Sixteenth Day of December, 2003

JAMES E. ROGAN
*Director of the United States Patent and Trademark Office*